United States Patent
Fisher et al.

(10) Patent No.: US 7,147,863 B2
(45) Date of Patent: Dec. 12, 2006

(54) UVA (> 360-400) AND UVB (300-325) SPECIFIC SUNSCREENS

(75) Inventors: Gary J. Fisher, Ypsilanti, MI (US);
John J. Voorhees, Ann Arbor, MI (US);
Sewon Kang, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 14 days.

(21) Appl. No.: 09/900,535

(22) Filed: Jul. 6, 2001

(65) Prior Publication Data

US 2002/0028185 A1 Mar. 7, 2002

Related U.S. Application Data

(60) Provisional application No. 60/216,244, filed on Jul. 6, 2000.

(51) Int. Cl.
 *A61K 7/00* (2006.01)
 *A61K 7/42* (2006.01)
 *A61K 31/07* (2006.01)

(52) U.S. Cl. ............... 424/401; 424/59; 514/725
(58) Field of Classification Search ........... 424/401, 424/59; 514/725
See application file for complete search history.

(56) References Cited

FOREIGN PATENT DOCUMENTS

| DE | 27 07 908 |     | 8/1978  |
| DE | 28 03 446 | A1  | 8/1979  |
| DE | 33 265 13 | A1  | 1/1985  |
| DE | 40 26 022 | A1  | 2/1992  |
| DE | 196 11 763| A1  | 10/1997 |

*Primary Examiner*—Vickie Kim
(74) *Attorney, Agent, or Firm*—Bradley N. Ruben

(57) ABSTRACT

UVB radiation of about 300–310 nm wavelength and UVA radiation of about 380–390 nm wavelength, each of which exists in solar light, induces MMPs (matrix metalloproteinases) in human skin that degrade the collagen of the dermal matrix. This degradation contributes to photoaging of human skin, which can be prevented by blocking these wavelengths of solar radiation. In contrast, diseases that result in the overproduction of collagen can be treated by exposing the affected with to radiation having wavelengths in those regions, for these wavelengths not only induce MMPs but also inhibit collagen biosynthesis. For lighter skinned people so affected, the UVA wavelengths are preferred because of the reduced amount of erythema, whereas dark skinned people can be treated with the UVB radiation because they generally do not suffer from erythema.

3 Claims, 17 Drawing Sheets

SOLAR SIMULATED LIGHT INDUCES cJUN IN HUMAN SKIN *IN VIVO*

SOLAR SIMULATED LIGHT ACTIVATES NF-κB IN HUMAN SKIN *IN VIVO*

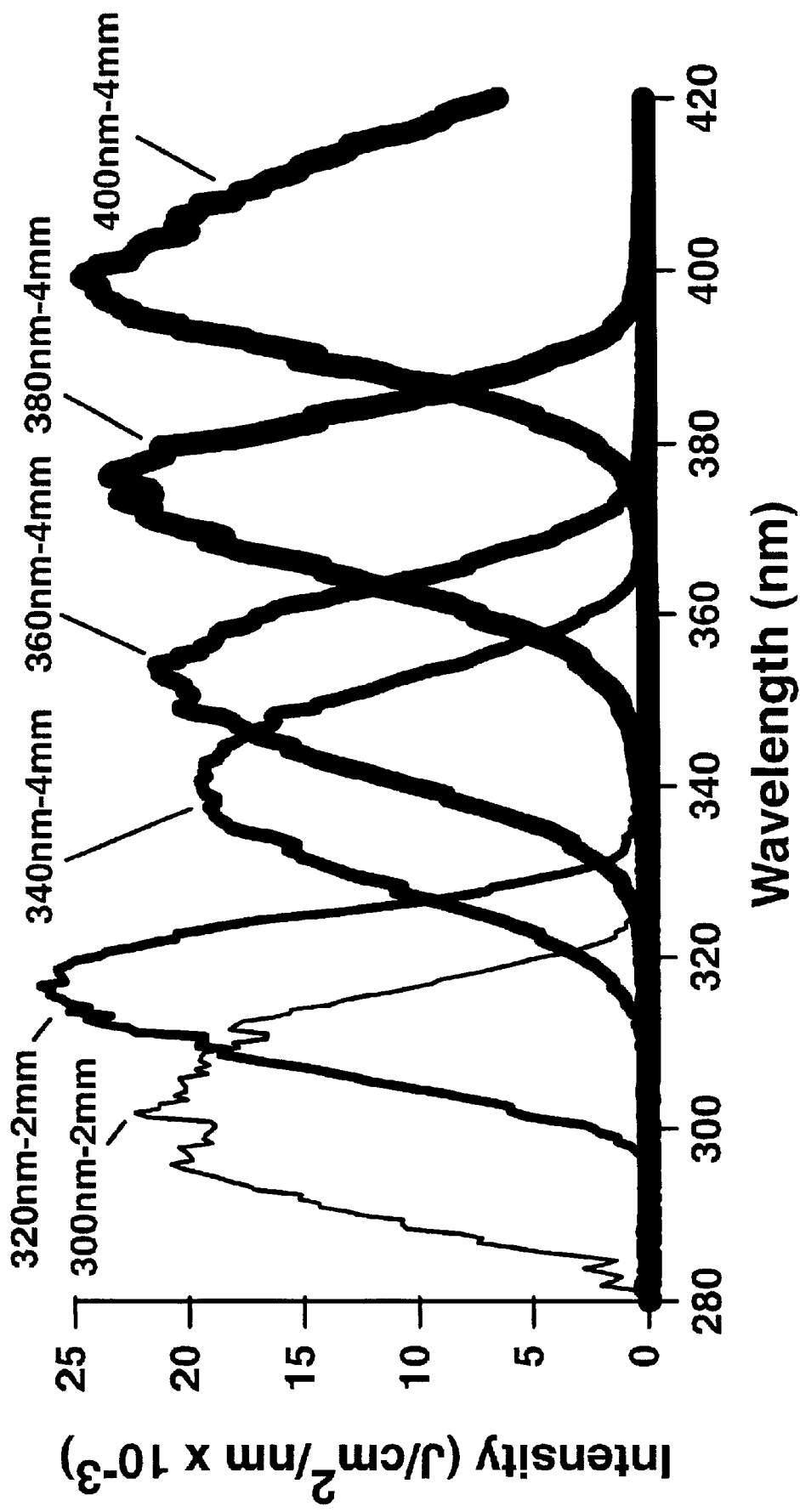

UVA (> 360-400) AND UVB (300-325) SPECIFIC SUNSCREENS

RELATED APPLICATIONS

This application is based on provisional application No. 60/216,244, filed Jul. 6, 2000, the disclosure of which is incorporated herein by reference.

BACKGROUND OF THE INVENTION

1. Field of the Invention

This invention relates to sunscreens that absorb specific wavelengths that we have found induce destructive enzymes in the skin, and to the use of these specific wavelengths in treating skin conditions.

2. The State of the Art

With regard to photodamage to skin from the sun, the prevailing view is now that both UVB and UVA radiation should be blocked to prevent damage to the skin. It has been known for some time that UVB, while enabling the skin to produce Vit. $D_3$, nevertheless also produces erythema (sunburn). If the UVB radiation reaches a threshold dose level termed the minimum erythemal dose (MED), then sufficient UVB radiation has been delivered to the skin to cause visible erythema. UVA radiation is orders of magnitude less erythmogenic than UVB radiation, but is nevertheless damaging to the skin. The art generally considers the damaging regions to be 280–320 nm for UVB, and 320–360 nm for UVA. UVB sunscreens are typically evaluated by their ability to prevent erythema, and that is how the Sun Protection Factor (SPF) is typically defined. Although less erythmogenic, UVA sunscreens are often tested in the same manner, or analogously to determine whether the compound screens against induction of pigment in the skin upon UVA exposure. See generally, *Sunscreens: Development, Evaluation*, and *Regulatory Aspects*, ed. by N. J. Lowe et al. (New York: Marcel Dekker, Inc., 1997), the disclosure of which is incorporated herein by reference.

Present sunscreen formulations now include a mixture of separate compounds for absorbing UVA and UVB radiation. Commercially approved preparations include a UVB blocker, such as a p-methoxycinnamate or an aminobenzoate, and a UVA blocker, such as a benzone or an anthranilate. These compounds generally absorb the incoming UV photon and reradiate a lower energy photon. While typically less cosmetically desirable, physical blockers, such as zinc oxide, generally provide better protection, at least in part because most people do not apply a sufficient amount of sunscreen, or apply it unevenly. In theory, an amount of 2 mg/cm$^2$ of sunscreen per skin area is to be applied to maintain the sun protection factor (SPF) value, although the amount typically applied in practice by individuals in recreational settings is much less.

The ideal compound would be one that absorbs well over the entire UVA/B spectrum, but no such compound has been identified to date. To further complicate matters, the solvent or medium in which the absorber is formulated will affect its absorbtion spectrum. While these shifts in absorbtion spectra can be qualitatively estimated, to some extent sunscreen formulation is an empirical art.

On the other hand, dermatologists have been resorting to the use of UVA and UVB radiation for the treatment of various skin conditions. UVB has been used for treating acne for some time. More recently, UVA radiation has been used for treating various dermatological fibrotic conditions: M. C. Polderman et al., "Ultraviolet A-I phototherapy for skin diseases," *Ned Tijdschr Geneeskd*, 1999 May 1, 143 (18):931–4; M. El-Mofty et al., "Low-dose broad-band UVA in morphea using a new method for evaluation," *Photodermatol Photoimmunol Photomed* 2000 Apr. 16(2):43–9; J. Dutz, "Treatment options for localized scleroderma," *Skin Therapy Lett* 2000, 5(2):3–5; J. W. Steger et al., "UVA therapy for scleroderma," *J. Am. Acad. Dermatol.*, May 1999, part 1, Vol. 40, No. 5.

SUMMARY OF THE INVENTION

Our prior patents and applications, such as U.S. Pat. No. 5,837,224 and our copending application Ser. No. 09/089,914, filed 3 Jun. 1998, and Ser. No. 09/285,860, filed 2 Apr. 1999, the disclosures of which are incorporated herein by reference, teach that UVB and UVA radiation induce matrix metalloproteinases (MMPs) in the skin which degrade the dermal collagen matrix, and that UVB and UVA radiation exposure causes a shutdown in collagen biosynthesis. We have now found specific radiation bands in the UVB and the UVA that induce MMPs.

Given these findings, one aspect of our invention is to provide a sunscreen that blocks these specific wavelengths, preferably about 285–325 nm in the UVB, most preferably about 295–315 nm in the UVB, and preferably from about 360 to about 400 nm in the UVA, most preferably from about 365 to about 395 in the UVA. While various commercially available UVB blockers adequately filter in this UVB range, those available for blocking UVA are less than desirable for blocking UVA radiation in this wavelength range.

Additionally, given these findings, UVA radiation between about 365 nm and about 395 nm can be used to treat fibrotic skin conditions in Caucasians and other light skin-colored people on whom it is less desirable to use UVB radiation because of the erythema. On the other hand, we have found that people with dark skin do not suffer significantly from erythema, although there is some skin reddening, and accordingly, UVB in the 295–315 nm wavelength range can be used for treating such conditions in these people.

BRIEF DESCRIPTION OF THE FIGURES

FIG. 5 shows overlaid the separate wavelengths we obtained using our solar simulator and various filters.

DESCRIPTION OF THE INVENTION

Figure 1:
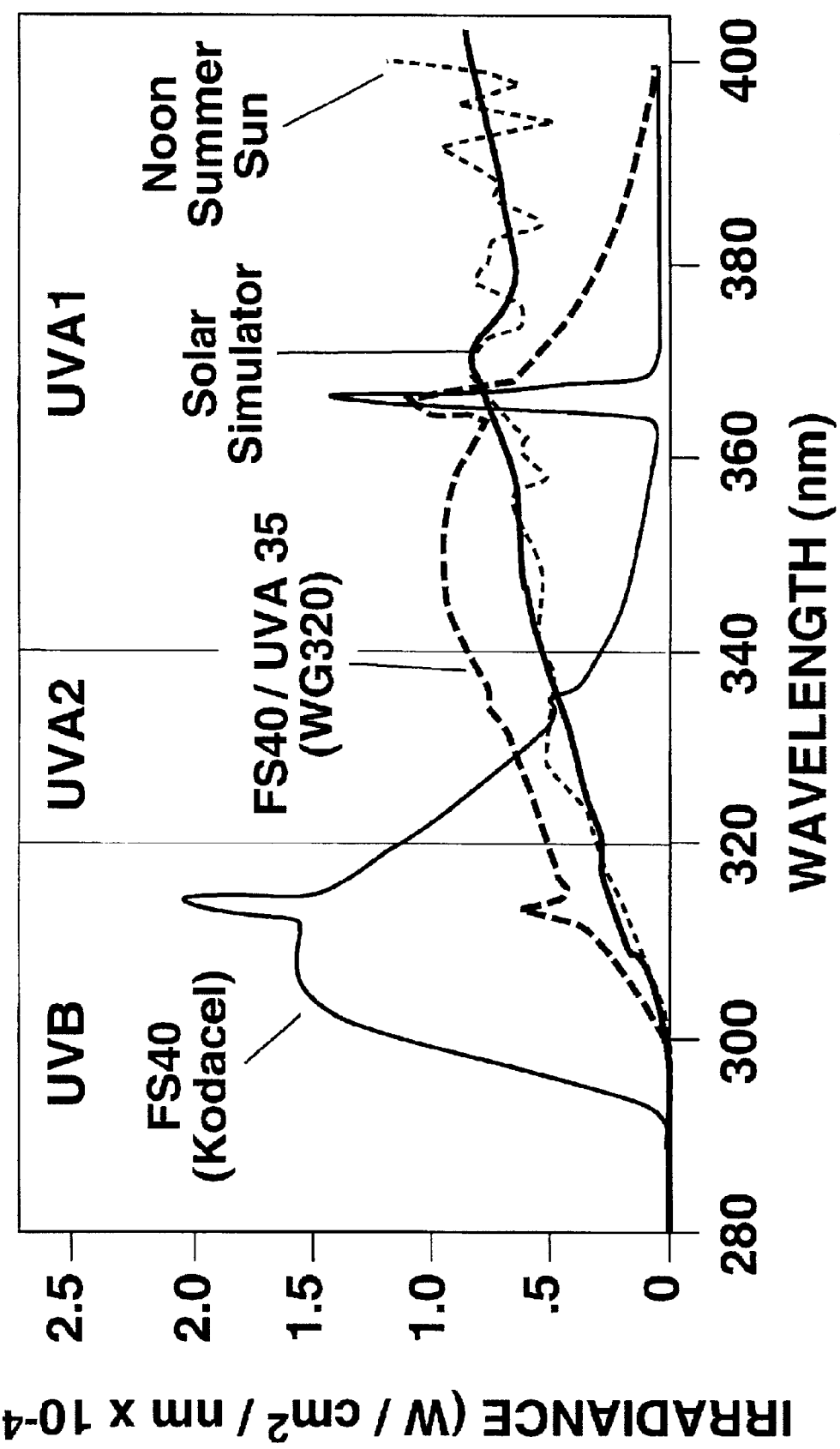
FIG. 1 depicts an overlay of the wavelength distributions of the noon summer sun, a solar simulator used in the following experiments, and an FS40 brand UV lamp filtered with a Kodacell or WG320 filter.

FIG. 1 depicts an overlay of the wavelength distributions of the noon summer sun, a solar simulator used in the following experiments, and an FS40 brand UV lamp filtered with a Kodacell or WG320 filter, all commercially available. As noted in the Background, present sunscreen philosophy is to filter the UVA wavelengths only up to about 360 nm. However, it can be seen that there is a significant irradiance at wavelengths above this region from natural sun. Accordingly, our solar simulator is also designed to deliver these wavelengths.

Figure 2A:
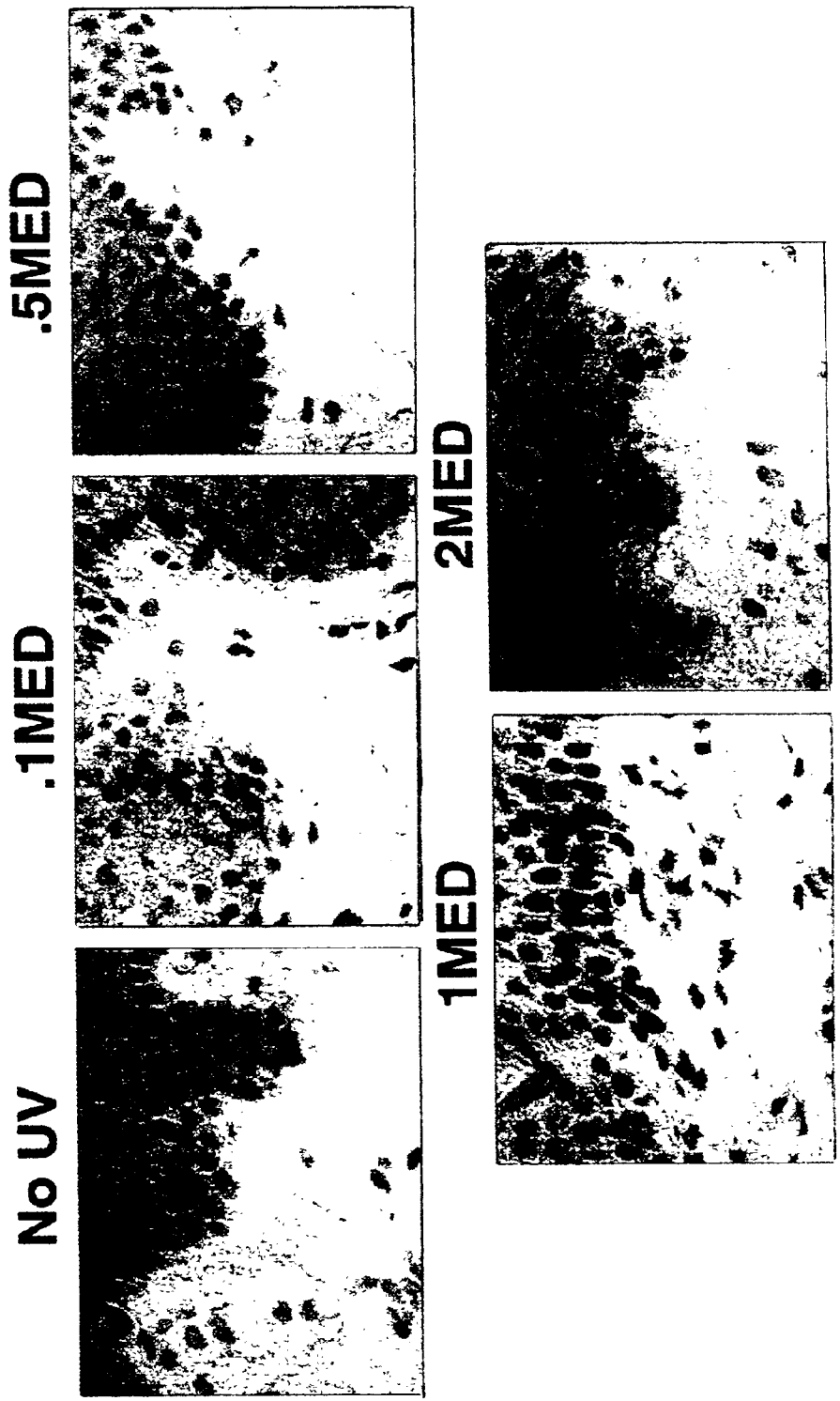
FIGS. 2A and 2B depict photomicrographs of stained human in vivo skin samples from subjects exposed to varying amounts of solar-simulated radiation, the amounts being defined by the resulting MED.
Figure 2B:
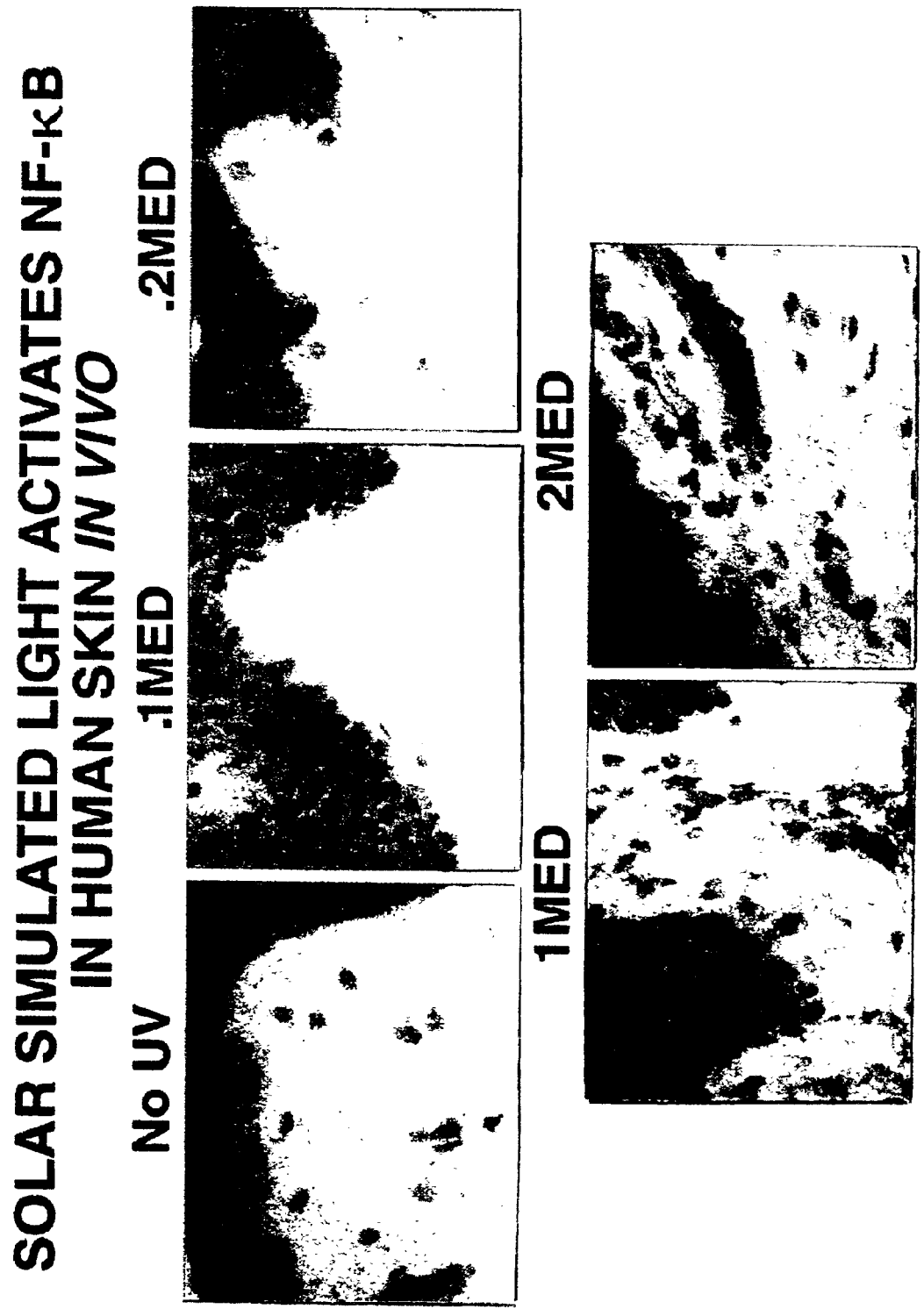

FIGS. 2A and 2B depict photomicrographs of stained human in vivo skin samples from subjects exposed to varying amounts of solar-simulated radiation, the amounts being defined by the resulting MED. The samples are stained for the presence of cJUN protein (FIG. 2A), a signalling compound that forms part of AP-1, and also stained for the presence of NF-κB (FIG. 2B), a transcription factor. Signalling involving each of AP-1 and NF-κB results in the presence of MMPs in the skin, by various mechanisms; MMPs are enzymes that degrade the collagen matrix of the dermis. As seen in these figures, at levels of one MED, and even lower, the amounts of these signalling compounds in the skin is increased due to irradiation.

Figure 3A:
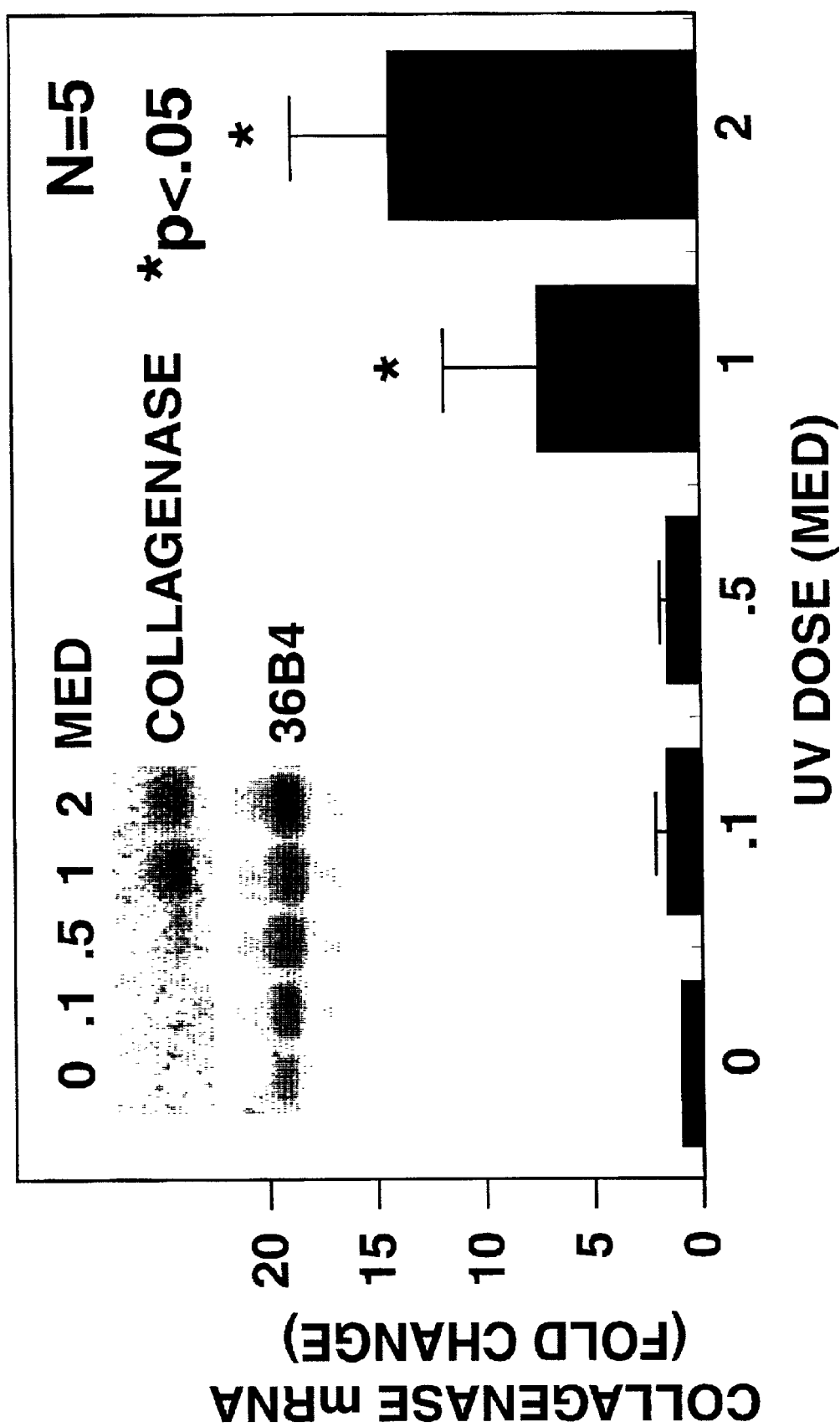
FIGS. 3A, 3B, and 3C depict the dose-dependent induction of collagenase (MMP-1)(3A) and the 92 kDa gellatinase (3B) as a function of MED, and the reduction in procollagen biosynthesis (3C) also as a function of MED, when using the solar simulator having the radiation profile as shown in FIG. 1.
Figure 3B:
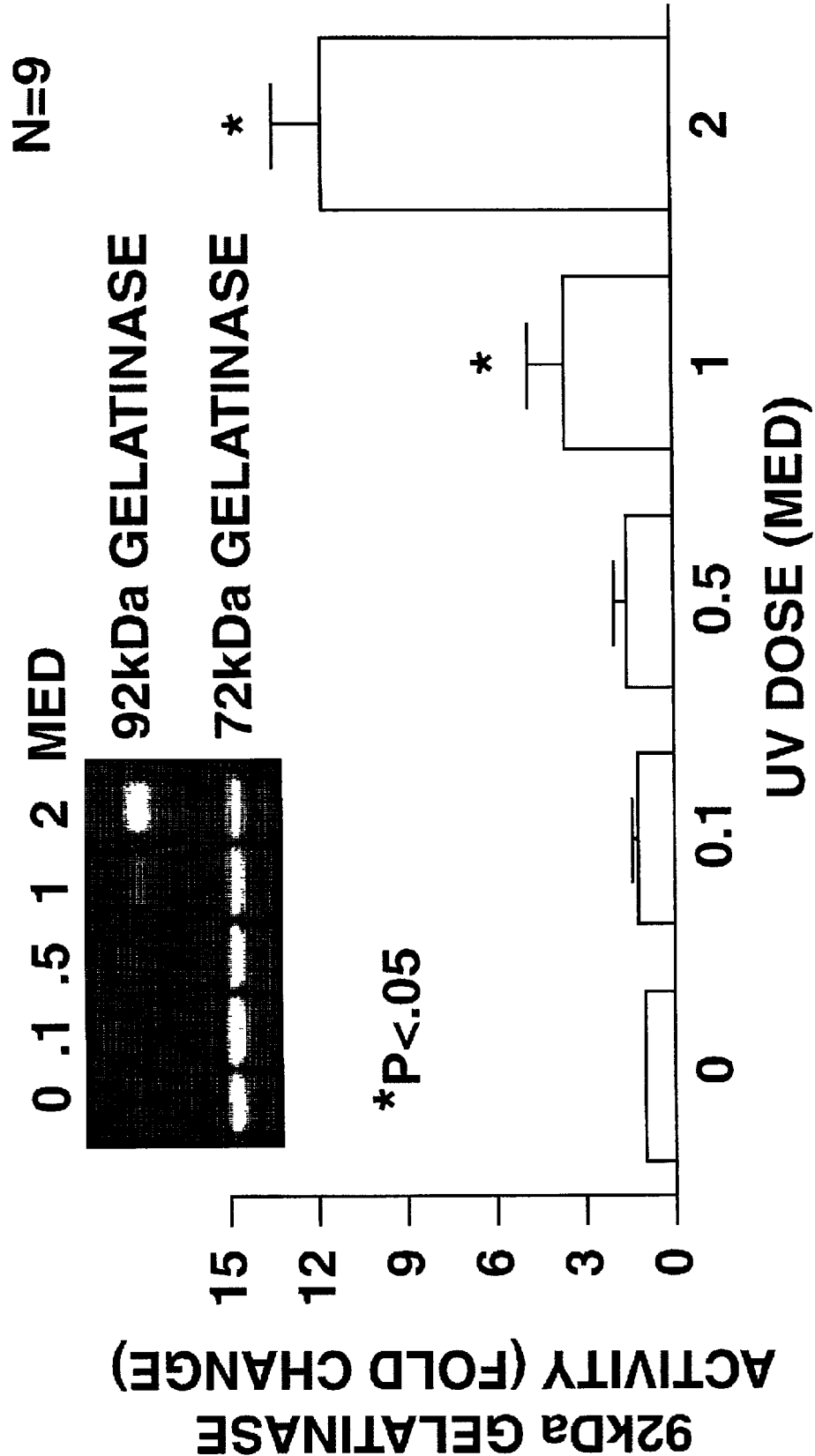
Figure 3C:
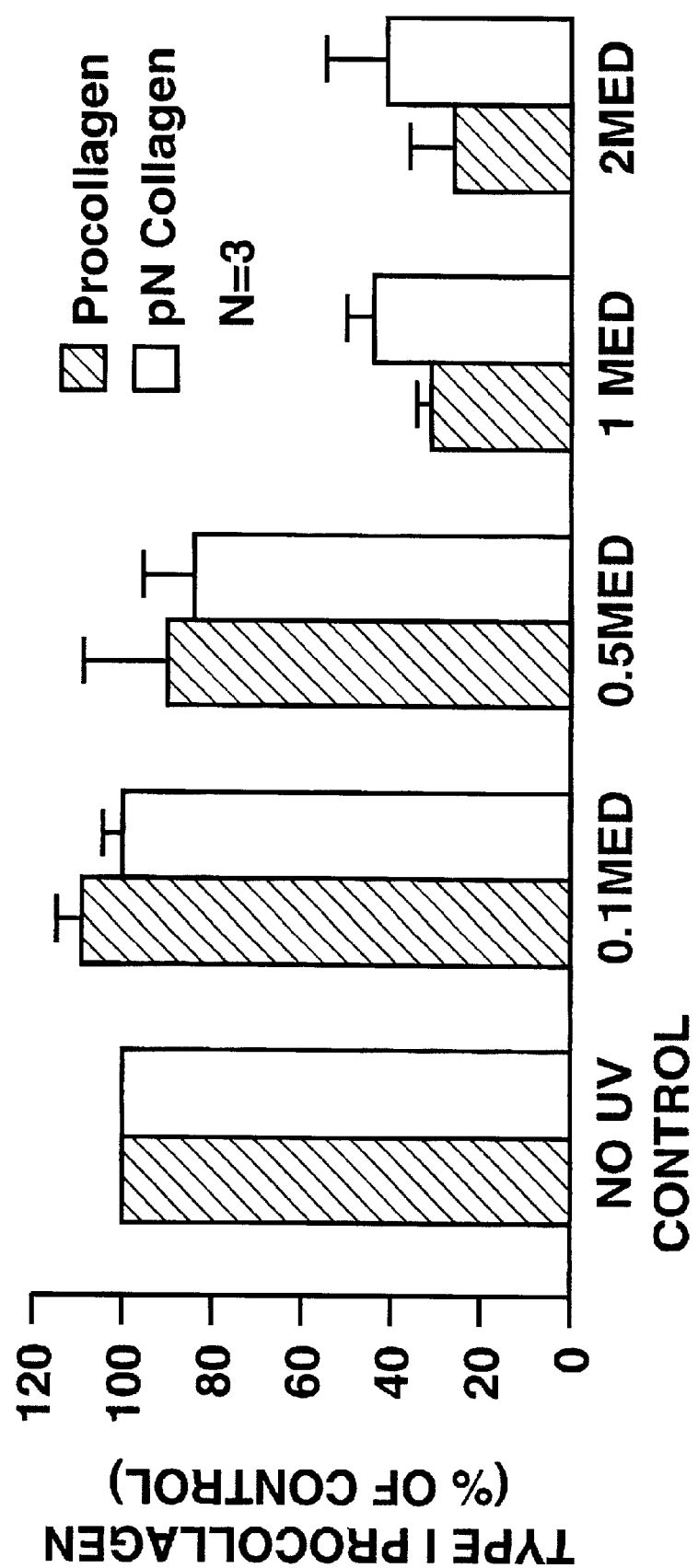

FIGS. 3A, 3B, and 3C depict the dose-dependent induction of collagenase (MMP-1)(3A) and the 92 kDa gellatinase (3B) as a function of MED, and the reduction in procollagen biosynthesis (3C) also as a function of MED, when using the solar simulator having the radiation profile as shown in FIG. 1. FIG. 3A shows a Northern blot of the collagenase, and the bar graph quantitatively shows the change in collagenase mRNA, which increases about 8 fold from the control (zero MED) upon irradiance with one MED, and to about 15 fold upon 2 MED. FIG. 3B shows similar results for UV-initiated induction of the 92 kDa gelatinase activity, increasing about 3 fold from the control with one MED, and about 12 fold with a dose of 2 MEDs. As explained in our prior patents and applications, UV irradiation of human skin induces the presence of enzymes that degrade the collagen matrix. Additionally as we have shown therein, the production of procollagen, the soluble precursor of collagen, is inhibited. As shown in FIG. 3C, procollagen product falls to about 30% of the control value after irradiation with one MED, and to about 20% of the control value after 2 MEDs. These results are obtained from human skin sampled between 8 hours and 48 hours after exposure to the UV radiation.

Figure 4A:
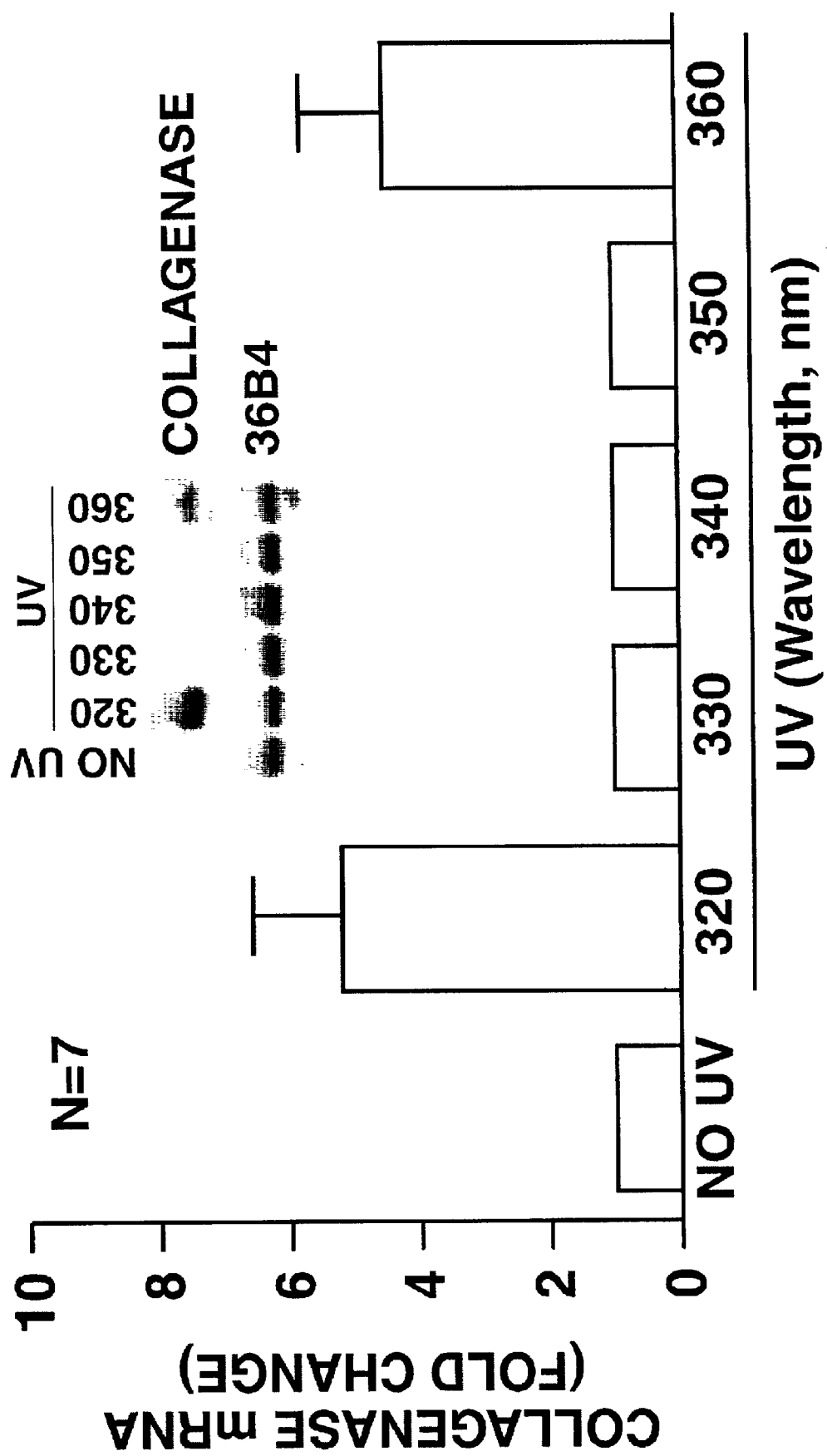
FIG. 4A depicts our results in determining the wavelength-related dependence of collagenase induction.
Figure 4B:
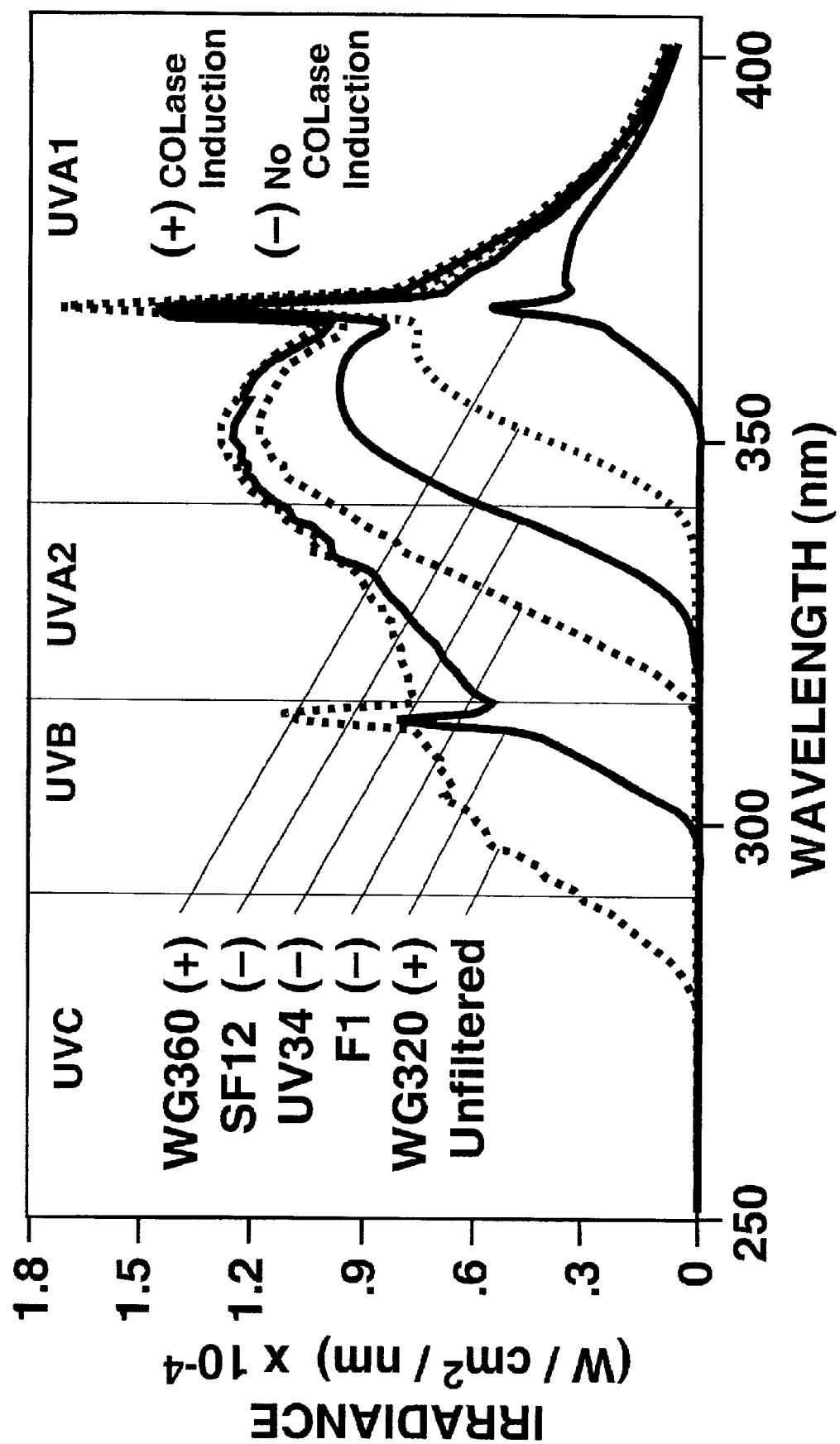
FIG. 4B shows the wavelengths transmitted through each of a number of different filters.

FIG. 4A depicts our results in determining the wavelength-related dependence of collagenase induction. Human volunteers' skin was irradiated with UV light transmitted through various filters to provide a range of wavelengths with which their skin was irradiated. When their UV-exposed skin was later biopsied, it was found that only wavelengths around 320 nm and above 360 nm were sufficient to induce collagenese at significant levels (at least a four fold increase in collagenase mRNA levels). These results are shown in FIG. 4A, where these two wavelengths were found to have induced significant increases in collagenase mRNA; the Northern blot for the collagenase mRNA is superimposed on the bar graph. FIG. 4B shows the wavelengths transmitted through each of a number of different filters. Experiments are performed so that the same amount of energy of the particular wavelength desired is delivered to the site, the energy being the area under the curve shown in FIG. 4B.

To more accurately determine what wavelengths are inducing MMPs, we used a series of fairly narrow wavelengths from our solar simulator, obtained using a monochomator, as shown in FIG. 5. Each wavelength has a fairly narrow band around its maximum at drops off rather steeply at ±20 nm from the peak.

Figure 6A:
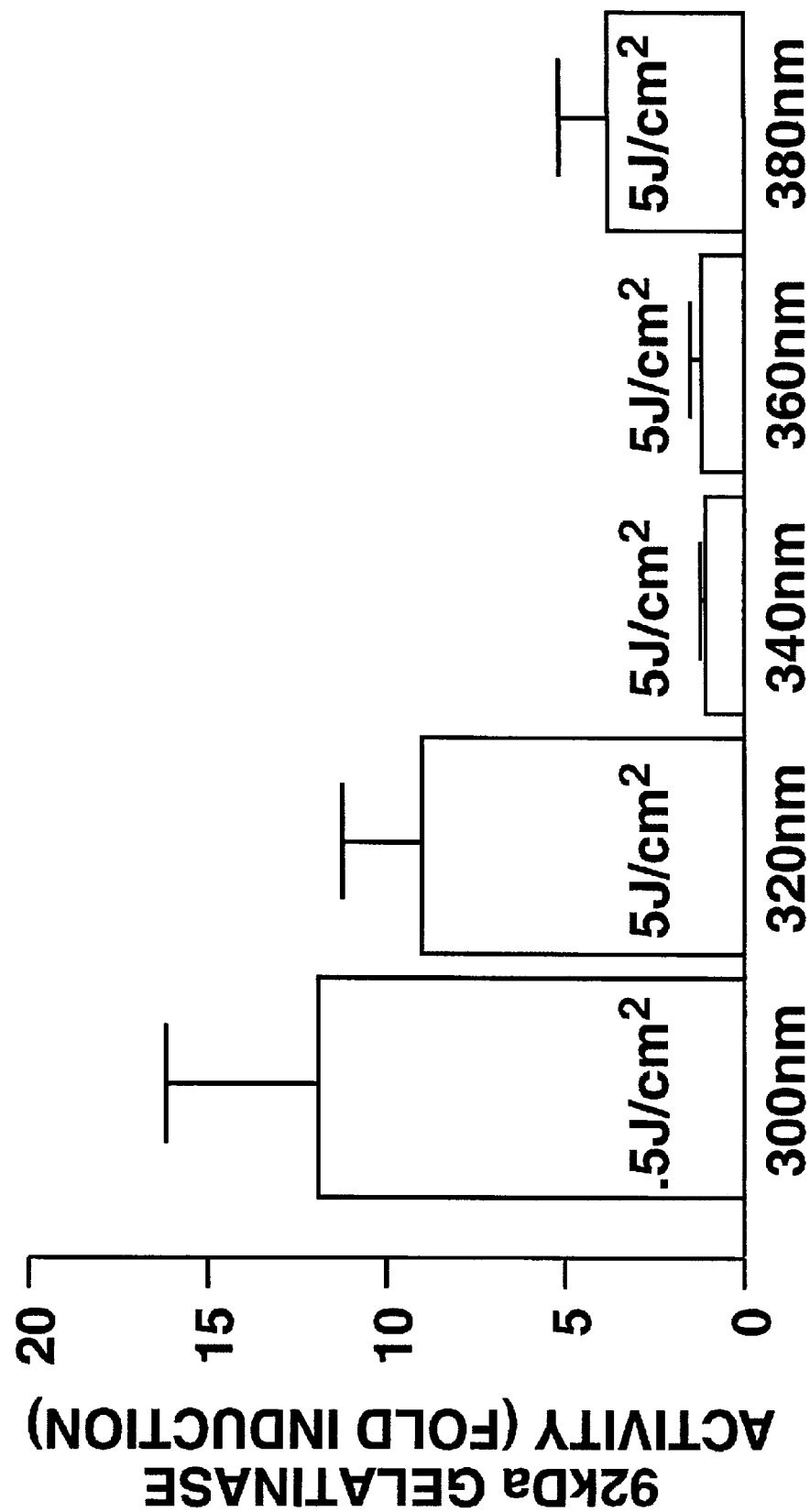
FIGS. 6A, 6B, and 6C depicts the induction of the 92 kDa gelatinase as a function of UV wavelength for various wavelength regions.
Figure 6B:
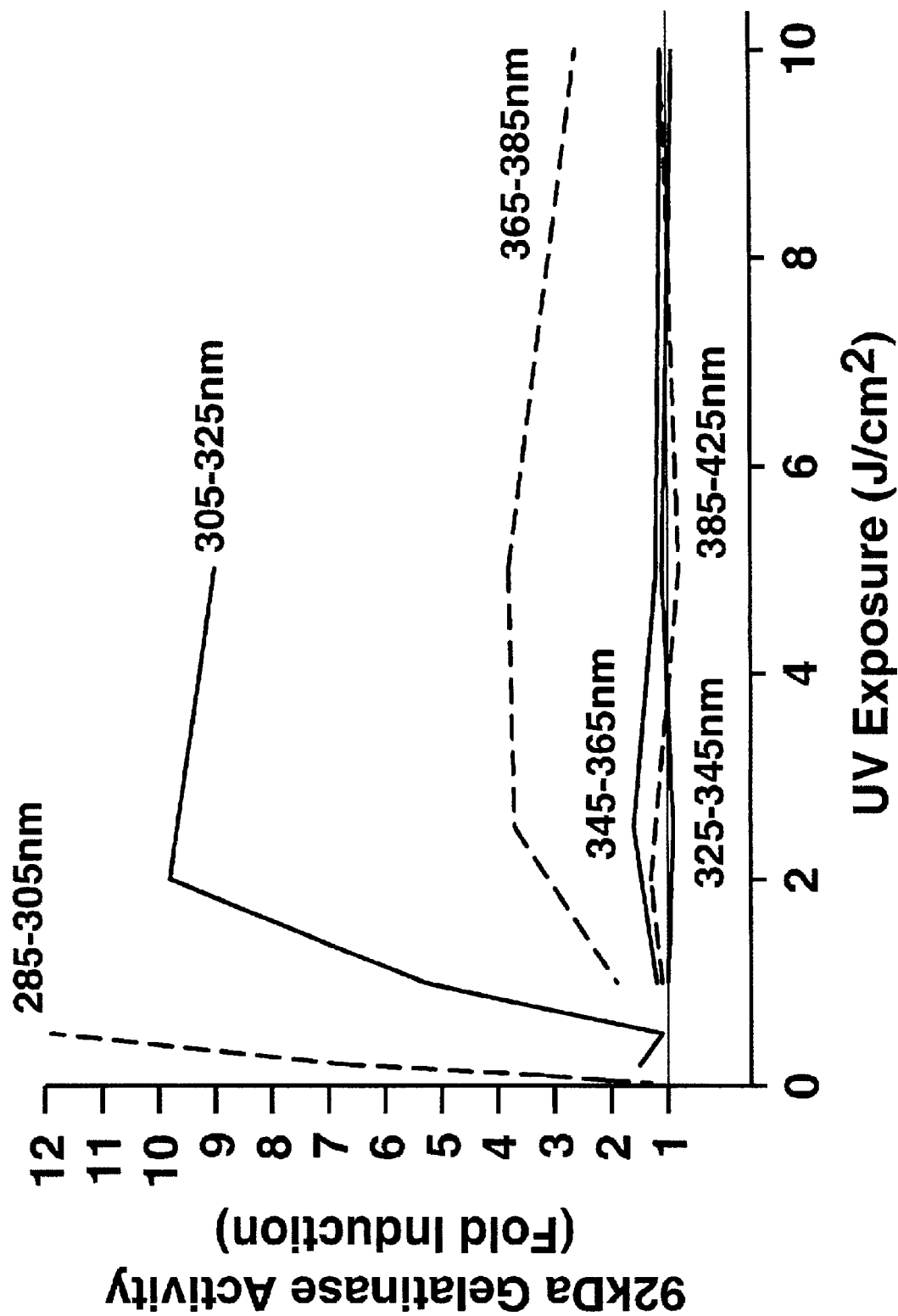
Figure 6C:
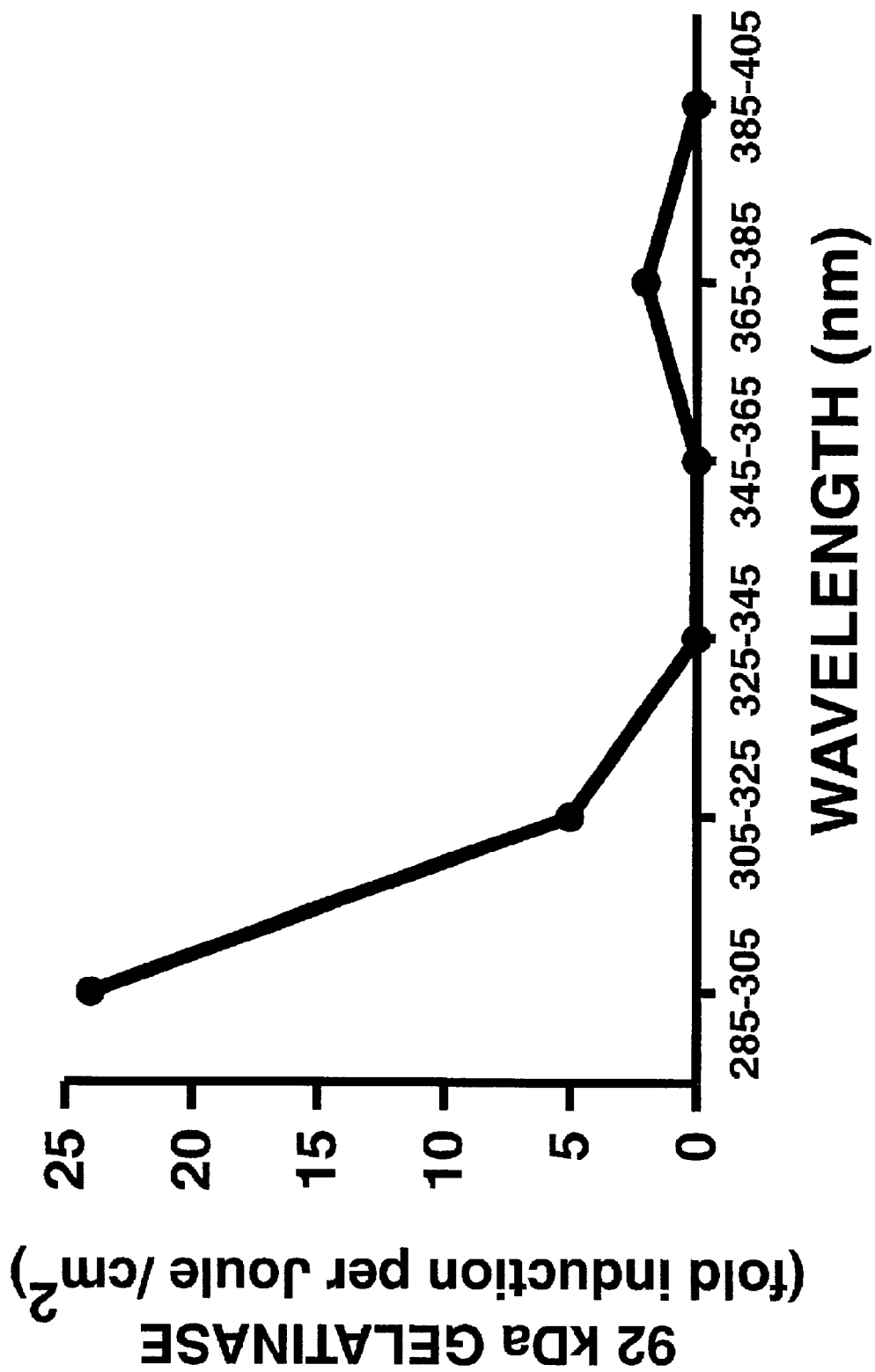

Using separately each of the transmitted wavelengths shown in FIG. 5, our human volunteers' skin was irradiated at comparable energies for each of five wavelengths corresponing to UVB, the border of UVB and UVA, UVA2, the border of UVA2 and UVA1, and UVA1. As shown in FIG. 6A, human skin irradiated with 0.5 J/cm$^2$ at 300 nm, and at 5 J/cm$^2$ at 320 nm and 380 nm, showed significant 92 kDa gelatinase activity above normal. Thus, these wavelengths clearly induce MMPs in human skin. Unexpectedly, irradiation at 340 nm and 360 nm, at the same energy levels as done with 320 nm and 380 nm, did not show any appreciable elevation in gelatinase activity. These results are unexpected based on the present philosophy in the industry of sunscreen production and formulation that only wavelengths up to 360 nm need be blocked to protect against the sun's harmful rays. This philosophy could be understood on the basis of the supposition that as the radiation wavelength approaches that of visible light the radiation is less likely to cause damage. However, our results clearly show that this supposition is incorrect and that UVA1 radiation above about 360 nm is sufficient and effective at inducing MMPs in human skin. FIG. 6B displays these results differently, as the fold induction in the 92 kDa gelatinase versus UV exposure for different wavelengths. The UVB range of 285–305 nm induces this gelatinase at relatively low energy levels. The upper UVB to lower UVA2 range of 305–325 nm induces MMPs up to ten fold rather quickly, and then levels off even as the energy input increases. While the induction level is not as great as those just mentioned, irradiating at 365–385 nm causes a rise in gelatinase induction to about four fold and then levels off. Again, and quite unexpectedly, irradiation at 325–365 nm and 385–425 nm did not appear to induce the 92 kDa gelatinase. Viewed in yet another way, FIG. 6C shows the wavelength dependence on the induction of the 92 kDa gelatinase: UVB light easily induces this degrading enzyme, and as the light increases to about 325 nm the induction falls precipitiously, except for a not insignificant "rise" from 365–385 nm where, again, the degrading enzyme is induced.

Figure 7:
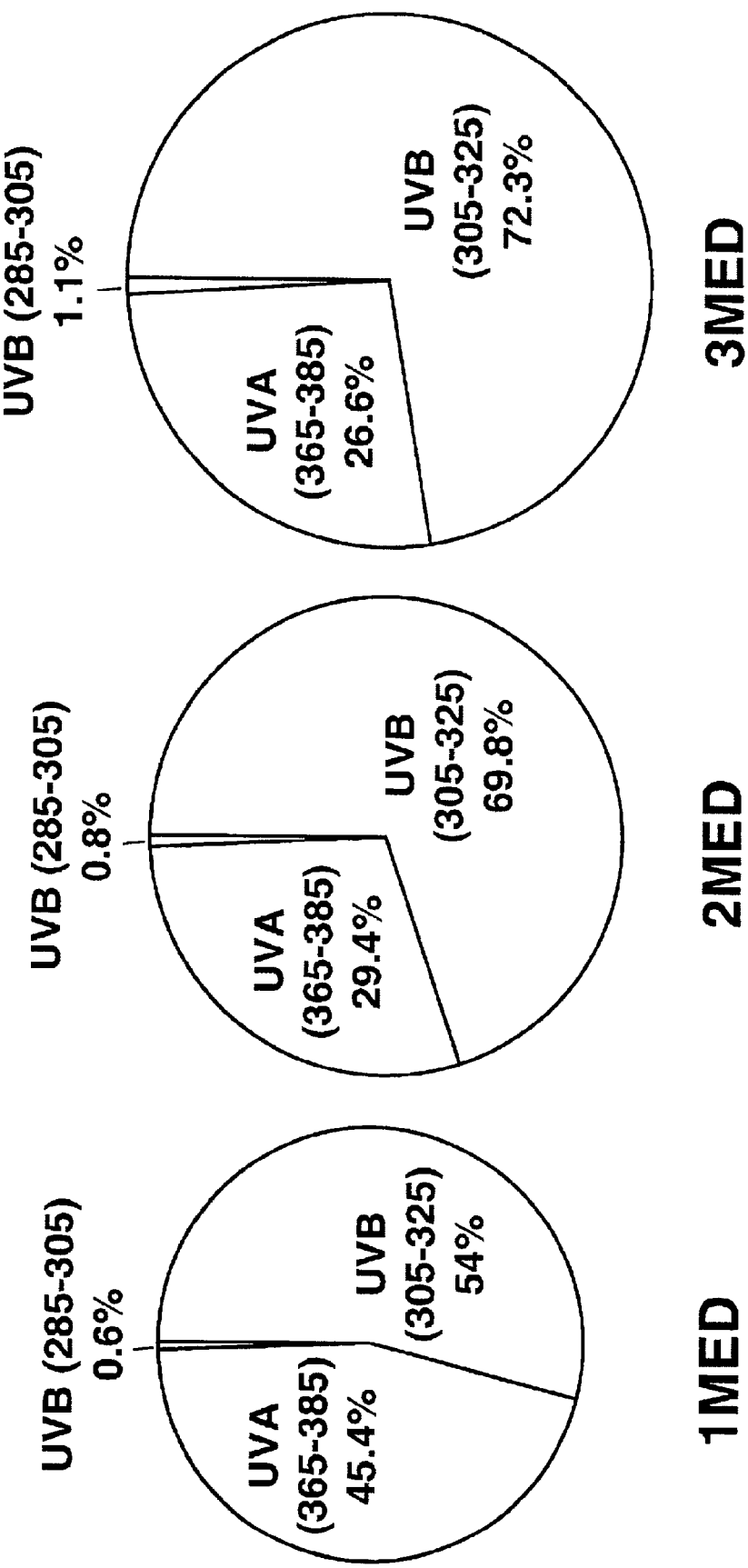
FIG. 7 depicts graphically the contribution of each of UVA and UVB to the induction of the 92 kDa gelatinase.

Based on these results, we have calculated the effective contributions of UVB and UVA radiation to inducing the 92 kDa gelatinase based on unfiltered radiation from our solar simulator. As shown in FIG. 7, exposure increases from one MED to three MEDs, the relative contribution of the UVA is almost halved, from about 45% to about 27%.

Figure 8:
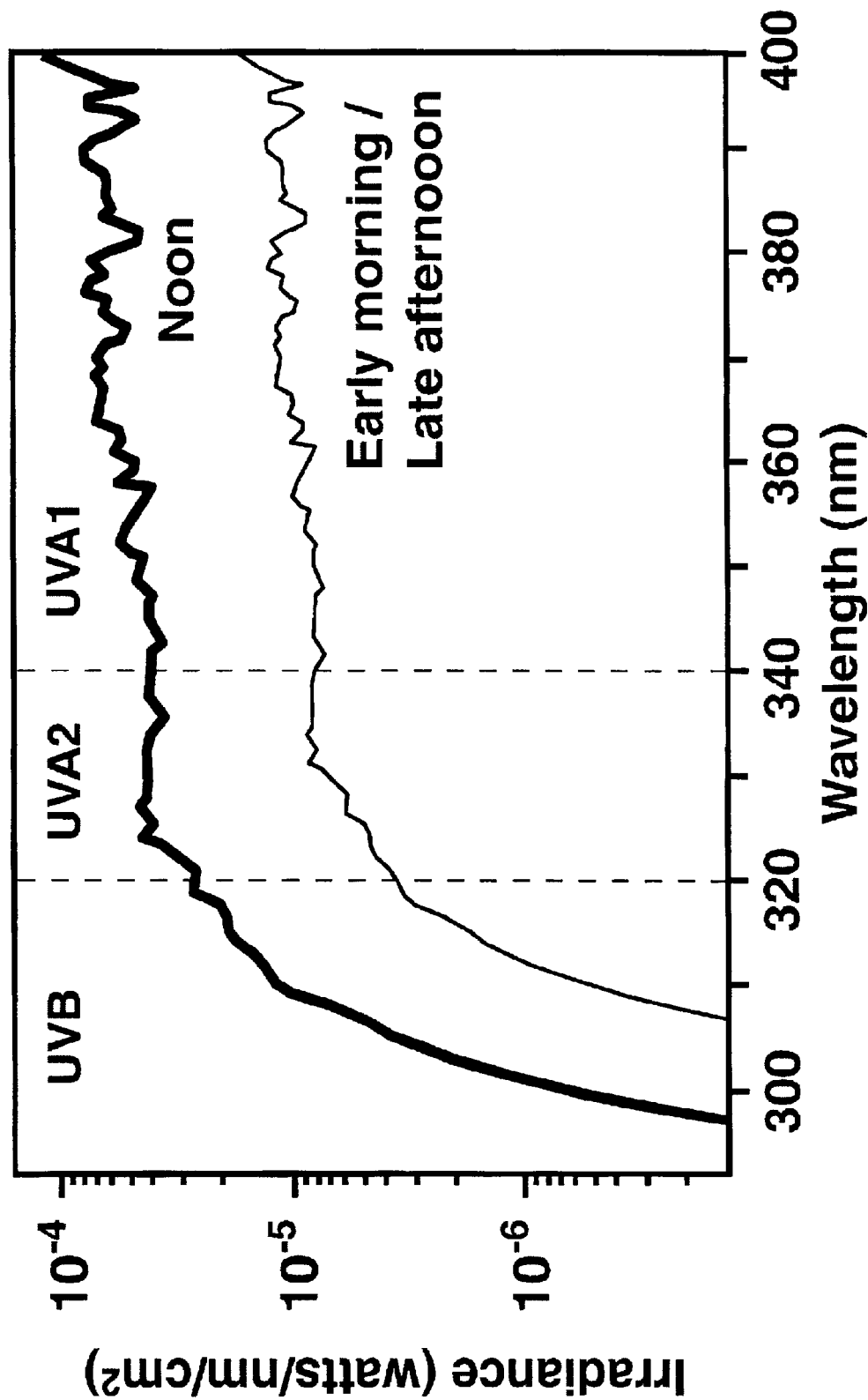
FIG. 8 depicts the variation in the irradiance of the sun between noon and either early morning or late afternoon.

As described in one of our co-pending applications, UVA radiation is harmful because it induces MMPs in human skin. From a marketing point of view, recreationists want to avoid sunburn, caused by UVB radiation, because it can destroy the joy of their recreation. UVB radiation is most prominent when the sun is at its zenith, and so typically that time of day is cautioned against for outdoor activities to minimize sunburn. However, the common belief is, therefore, that earlier and later times of day are not bad for one's skin because it is much more difficult to get a sunburn at 7 am or 5 pm. FIG. 8 shows the irradiance of sunlight versus wavelength for two different times of day: noon and early morning/late afternoon. As seen, a significant portion of the sun's UVB radiation reaches the earth's surface at noon, and so the conventional wisdom to avoid the noon sun, primarly because of increased risk of sunburn, appears valid. There is signicantly less UVB radiation from the early morning or late afternoon sun that reaches the earth's surface, and the wavelengths below about 295 nm are competely absent. Nevertheless, the UVA portion, while decreased on the order of half a magnitude, is still present and available to damage the skin, even though there is insufficient UVA radiation to cause erythema.

Figure 9:
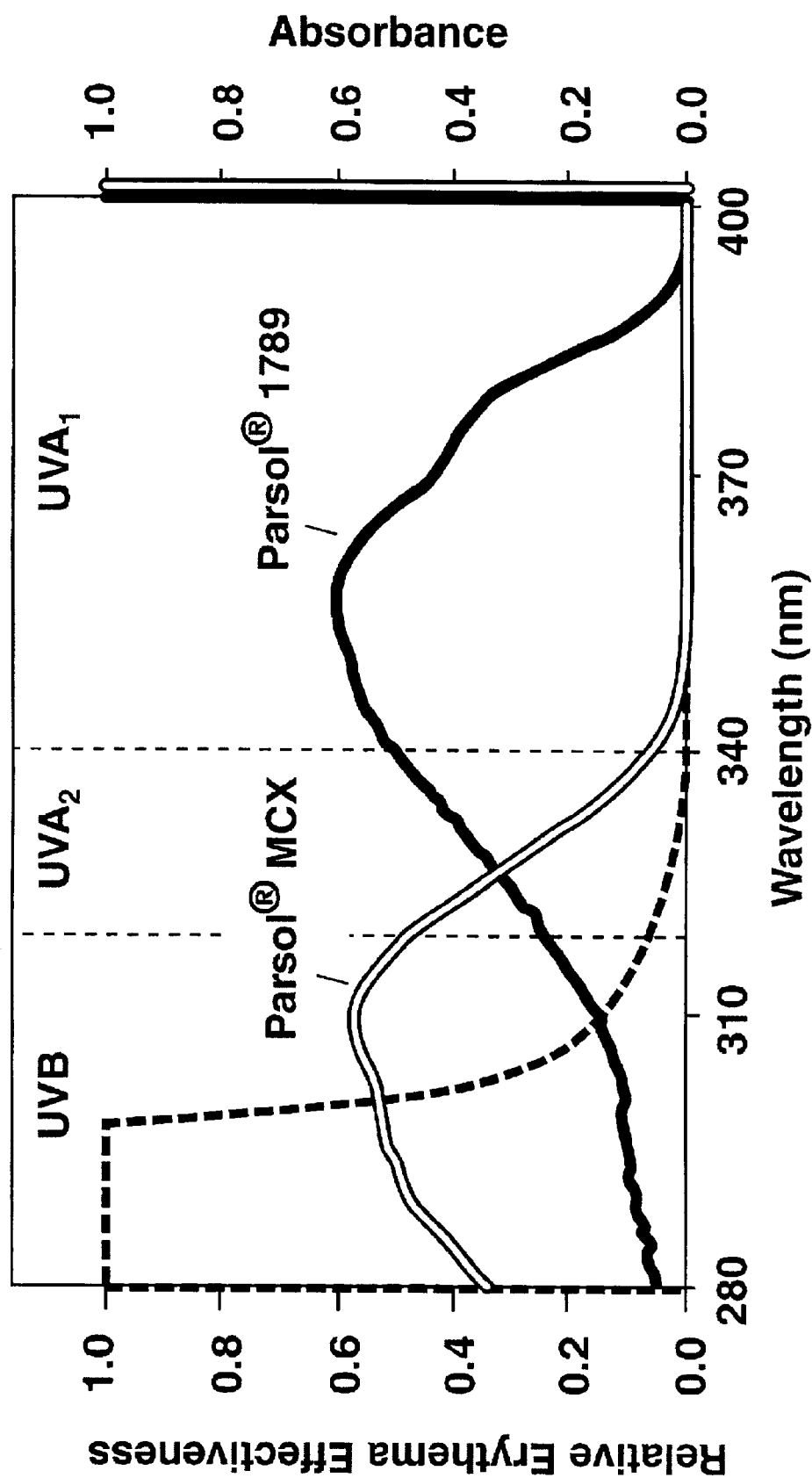
FIG. 9 depicts the UV absorbance of two specific sunscreen compositions.
Figure 10:
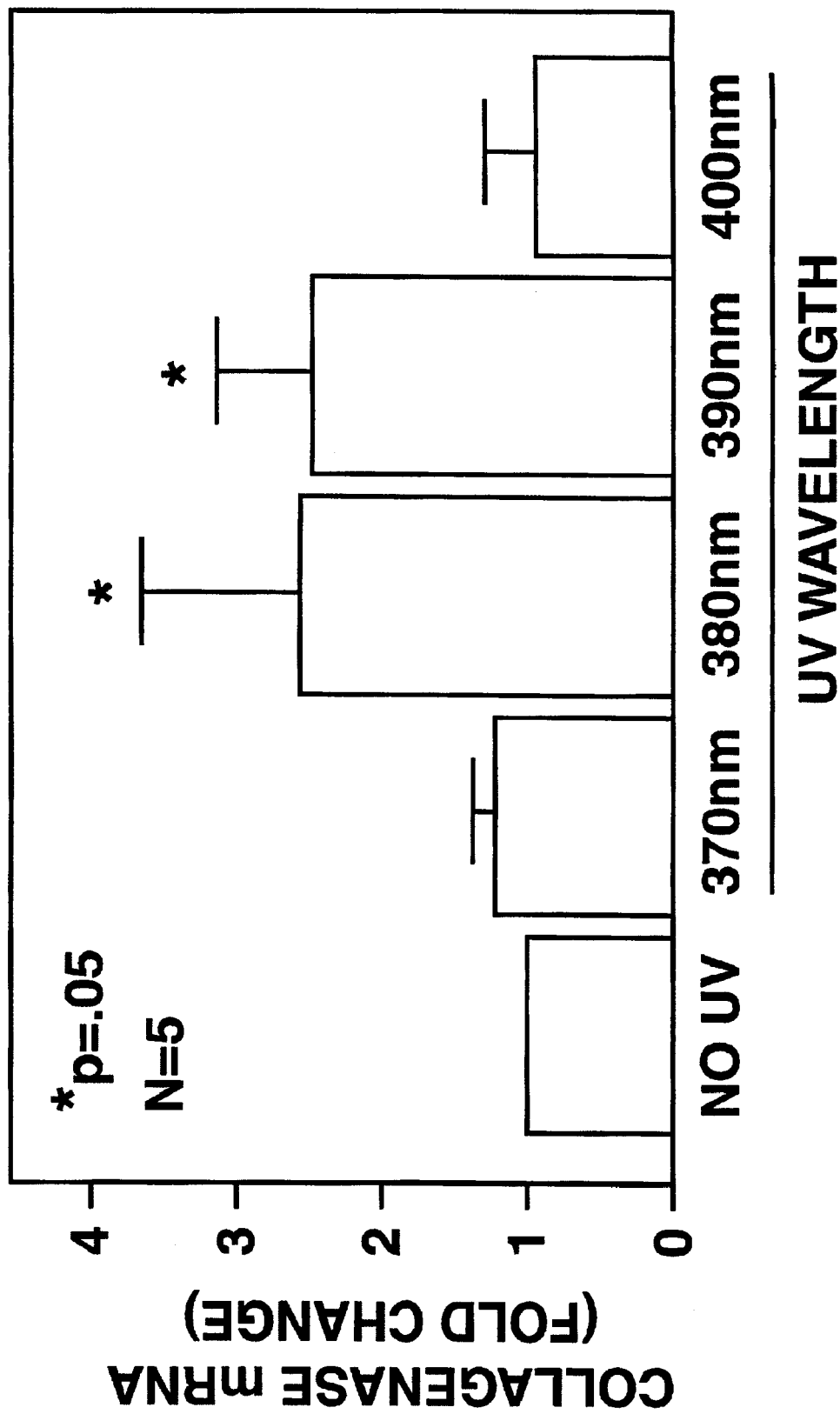
FIG. 10 depicts the induction of collagenase mRNA as a function of UV wavelength in the UVA region.

Thus, to adequately protect human skin from the UV-induced enzymes that degrade the collagen matrix, and which inhibit collagen biosynthesis, a sunscreen formulation must block both radiation of less then 325 nm and that between about 360 nm and 400 nm. In our prior application Ser. No. 09/089,914, we proposed a sunscreen comprising a UVB blocker such as PARSOL MCX and a UVA blocker such as PARSOL 1789. The protection afforded by this combination is shown in FIG. 9. Other UVB blockers known in the art, and in light of the information provided herein, are also suitable. However, various UVA blockers, including PARSOL 1789 and various others such as TINOSORB brand blockers (available from Ciba, Basel, Switzerland) are relatively broadband blockers and while blocking some of the UVA radiation in the >360–400 nm range, are not optimized for that region. As shown in FIG. 9, PARSOL 1789 appears adequete in the UVA1 area of 340–360 nm, falls off at 370 nm, falls off dramatically to 380, and has almost no absorbance in the area of 390–400 nm. However, as shown in FIG. 10, irradiation of human skin with 380 nm or 390 nm results in significant collagenase induction. As noted above, these wavelengths are greater than what the 360 nm the industry desires to block with its compounds, because it is generally believed that a broad band absorber will provide the desired blocking effects. To the contrary, we have shown that it is sufficient to block narrow bands of UV radiation, namely 295–325 nm in the UVB, more preferably 305–325 nm, and those wavelengths above 360 nm in the UVA, and that blocking these wavelengths achieves the desired prevention of UV-induced inhibition of MMPs in human skin.

Figure 11:
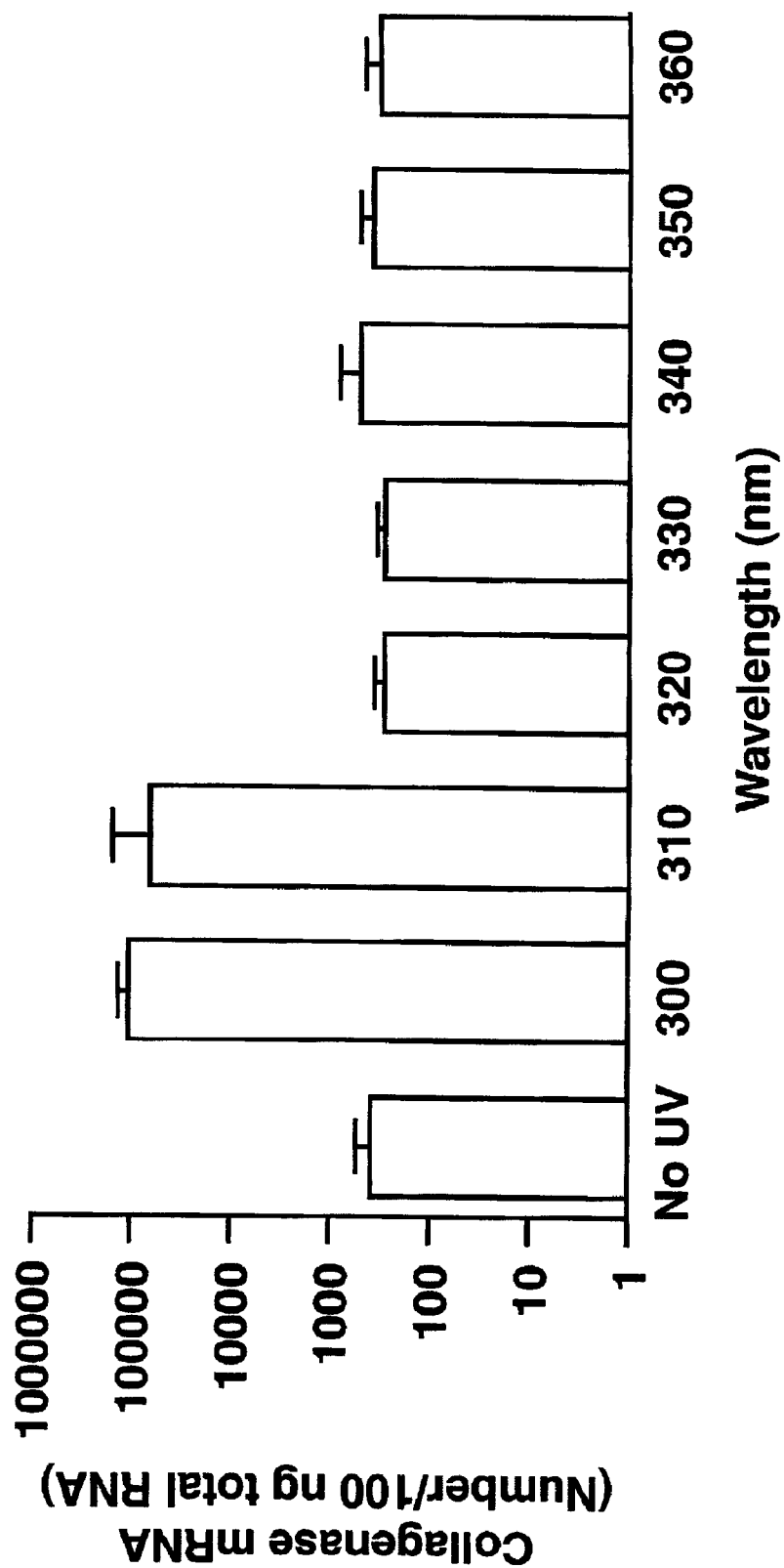
FIG. 11 depicts the induction of collagenase mRNA as a function of UV wavelength in the UVB region.

FIG. 11 depicts the results, in sampled human skin exposed to each of the separate wavelengths shown on the x-axis, of the amount of collagenase mRNA induced by each of those wavelength regions (as number of collagenase mRNA molecules per 100 ng of total RNA). As shown in FIG. 11, at 310 nm and 320 nm, collagenase mRNA was induced at levels some two orders of magnitude greater than the level sampled from non-UV exposed skin (e.g., 353 with no UV versus 105,000 at 300 nm and 67,000 at 310 nm). Clearly, there is a significant dependence on wavelength for collagen induction.

It may be difficult to formulate a cosmetically acceptable sunscreen for the upper UVA1 region. As described by N. A. Shaath in *Sunscreens* (op cit.; Chpt. 15), chemical sunscreens, as opposed to physical sunscreens like zinc oxide and titanium oxide, absorb a photon and reradiate the energy as a longer wavelength: very low energy wavelengths over 800 nm as heat (which is small compared with the heat input to the skin from the sun); intermediate energy wavelengths in the visible region (fluorescence), and/or low UV wavelengths (380–450 nm). A sunscreen that appears to fluoresce may be cosmetically unacceptable. Additionally, physical sunscreens can be cosmetically unacceptable because of their whitish appearance. Based on our findings, it will be important to assure that the energy is not reradiated in the region of >360–400 nm, for both UVA sunscreens and UVB sunscreen. Thus, a presently available sunscreen, whether a UVB or a UVA blocker, may reradiate in the region of >360 nm to 400 nm that we have found is harmful to the collagen matrix of the skin.

To formulate a desirable sunscreen, a chemist of ordinary skill in the sunscreen art will first make estimates of the structure of the compound required to absorb in the desired wavelength region, the structure typically focusing on the number and type of conjugated bonds, the presence and/or absence of electron-stabilizing groups, and the like. The candidate compound is then tested in a spectrophotometer to determine at which wavelength(s) it absorbs light (UV here), and then, preferably according to this invention, at what wavelengths the absorbed light is re-radiated. As noted, the vehicle/medium in which the compound is dispersed will affect the wavelengths absorbed. For example, for acidic compounds dispersed in an alkaline medium, the medium assists in the formation of anions that tend to increase delocalization of electrons, thereby decreasing the energy required for the electronic transition in the UV spectrum (a "bathochromic" shift to longer wavelengths, here towards the 400 nm range). Likewise, a not strongly polar compound may have an excited state that adds to the molecule's polarity, in which case a polar solvent stabilizes the transition state and a bathochomic shift to longer wavelengths occurs. The more efficient the electron delocalization, the higher the extinction coefficient of the compound. Although it is most desirable to have an absorbtion maximum $\lambda_{max}$ and extinction coefficient ($\epsilon$) not affected by the solvent(s), the medium may be used advanatageously. A molecule may absorb and re-radiate only a few times before it is destroyed, or it may be able to do this many times before being degraded. The efficiency of a candidate sunscreen molecule at absorbing light of a desired wavelength is its extinction coefficient. Further, for a compound that is perhaps less efficient than desirable, it is beneficial to put as much of the compound in the composition to the extent that it does not cause burning or stinging of the skin, is not toxic, and the like. Still further, as mentioned above, these organic compounds typically re-radiate the energy absorbed, sometimes in the infrared, and sometimes in the visible (and sometimes in the low UV region, which we have found is detrimental). While many would not consider a fluorescing compound to be cosmetically acceptable, children, teens, and others may likely consider such a compound as stylish. Further, the use of a compound that re-radiates in the visible spectrum would aid in determining whether a sufficient amount of the compound has been applied, and whether the coverage is complete (e.g., non-covered areas would not fluoresce). Additionally, if the fluorescence is not very strong, it is less likely that it would be seen in full sunlight.

These sunscreen compounds can also be provided in garments and textiles. They can be provided as a finish on the fiber that is later woven, or as a coating on the fiber or fabric that is later cured or set. The sunscreen molecule can be provided as a conjugate; that is, attached to a molecule having a portion that is attracted to the fiber. Of course, depending on the fabric (cotton, polyester, nylon), different conjugates, or multifunctional conjugates, would be required.

One benefit to our present findings is a better methodology for treating fibrotic skin conditions. Examples of such conditions, without being limited thereto, include morphea, scleroderma, burn scars, hypertrophic scars (due to any skin injury), keloids, Dupuytren's Contractures (e.g., Peyronie's disease, trigger finger), acne scars, stretch marks, and the like. For conditions in which there is excess collagen, the present invention provides the knowledge that irradiation with specific wavelengths of UV radiation induces MMPs to degrade the excess collagen and thereby help the patient heal himself. Because Caucasians and light-skinned people are prone to sunburn, treatment of such conditions is preferably with UV radiation in the range of about 365–395 nm. As shown in our prior patent and applications, MMP levels remain elevated for 48 hours or even longer after exposure to at least one MED of UV radiation, and collagen biosynthesis is similarly inhibited. Accordingly, treatment of a patient with 5–50 $J/cm^2$ of 365–395 nm UV radiation a few times a week is likely to be effective. On the other hand, we have discovered that dark-skinned people are generally not effected with erythema (but excluding light skinned blacks, who are susceptible to erythema). Accordingly, these people can be treated with UVB radiation, which is more effective at inducing MMPs and inhibiting collagen biosynthesis at lower energy doses; the same treatment schedule should likely function as well. Further, based on our findings, present technology for developing lasers can be used to tailor a laser to provide radiation at the desired wavelength depending upon the person's normal skin color. A person's skin darkness can be measured, for example, with a Minolta Color Meter model CR-200 chromameter. This chromameter provides as its output a number, wherein a lower number indicates lower skin reflectance of light and thus a darker skin color (L* scale being lower for darker skin). As used herein, dark skinned persons generally have an L* value of less than 55.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A method for improving the manufacture of a sunscreen comprising determining the absorbance of a candidate compound for UV wavelengths of 280–360 nm when the candidate compound is dispersed in a given medium, and then determining whether said candidate compound re-radiates UVA in the region of greater than about 360 nm to about 400 nm upon exposure to sunlight, and if so, rejecting said compound for use in said sunscreen.

2. The improved method of claim 1, wherein the UVA range is about 370–390 nm.

3. The improved method of claim 1, further comprising admixing a first candidate compound that does not re-radiate in the region of greater than about 360 nm up to about 400 nm with a second compound that absorbs radiation in the range of about 310–320 nm, admixing said first and second compounds in a suitable carrier, and providing said admixing in a dispensing container.

* * * * *

UNITED STATES PATENT AND TRADEMARK OFFICE
CERTIFICATE OF CORRECTION

PATENT NO. : 7,147,863 B2  Page 1 of 1
APPLICATION NO. : 09/900535
DATED : December 12, 2006
INVENTOR(S) : G. Fisher, J. Voorhees and S. Kang It is certified that error appears in the above-identified patent and that said Letters Patent is hereby corrected as shown below:

Column 8, lines 26-27, delete "admixing" and replace with --admixture--.

Signed and Sealed this

Tenth Day of April, 2007

JON W. DUDAS
*Director of the United States Patent and Trademark Office*